United States Patent
Mignucci et al.

(10) Patent No.: US 8,562,621 B2
(45) Date of Patent: Oct. 22, 2013

(54) ANTERIOR SPINAL INTERBODY FUSION DELIVERY SYSTEM

(75) Inventors: Luis A. Mignucci, Plano, TX (US); Kenneth R. Konya, Lexington, TX (US); Willie A. Janecka, Jr., Georgetown, TX (US)

(73) Assignee: Luis A. Mignucci, Plano, TX (US)

( * ) Notice: Subject to any disclaimer, the term of this patent is extended or adjusted under 35 U.S.C. 154(b) by 554 days.

(21) Appl. No.: 11/825,467

(22) Filed: Jul. 6, 2007

(65) Prior Publication Data

US 2009/0012527 A1 Jan. 8, 2009

(51) Int. Cl.
*A61B 17/58* (2006.01)
*A61B 19/00* (2006.01)

(52) U.S. Cl.
USPC ........................................................... 606/99

(58) Field of Classification Search
USPC .............................. 606/86 A, 90, 96, 99, 105; 623/17.11–17.16
See application file for complete search history.

(56) References Cited

U.S. PATENT DOCUMENTS

| | | | |
|---|---|---|---|
| 6,551,316 B1 * | 4/2003 | Rinner et al. | 606/57 |
| 6,616,671 B2 * | 9/2003 | Landry et al. | 606/99 |
| 6,648,895 B2 * | 11/2003 | Burkus et al. | 606/90 |
| 6,652,533 B2 * | 11/2003 | O'Neil | 606/100 |
| 6,712,825 B2 * | 3/2004 | Aebi et al. | 606/90 |
| 6,716,218 B2 * | 4/2004 | Holmes et al. | 606/105 |
| 7,004,947 B2 * | 2/2006 | Shluzas et al. | 606/105 |
| 7,081,118 B2 * | 7/2006 | Weber et al. | 606/90 |
| 7,169,153 B2 * | 1/2007 | Keller | 606/99 |
| 7,465,305 B2 * | 12/2008 | Liu et al. | 606/84 |
| 7,608,080 B2 * | 10/2009 | Shipp et al. | 606/99 |
| 2003/0149438 A1 * | 8/2003 | Nichols et al. | 606/99 |
| 2003/0225416 A1 * | 12/2003 | Bonvallet et al. | 606/105 |
| 2006/0036258 A1 * | 2/2006 | Zucherman et al. | 606/90 |

FOREIGN PATENT DOCUMENTS

| | | |
|---|---|---|
| DE | 202005016360 | 2/2006 |
| WO | WO 03/099146 | 12/2003 |
| WO | WO 2007/018457 | 2/2007 |
| WO | WO 2008/073185 | 6/2008 |

OTHER PUBLICATIONS

International Search Report and the Written Opinion from PCT/US2008/083300, mailed May 11, 2008.

* cited by examiner

*Primary Examiner* — Kevin T Truong
*Assistant Examiner* — Christopher Beccia

(57) ABSTRACT

A method includes providing a surgical instrument comprising a clear passageway, a first stationary finger, a first adjustable finger, and a first pull nut; inserting the first stationary finger and the first adjustable finger between two vertebrae; rotating the first pull nut with a hex drive, thereby separating the first adjustable finger from the first stationary finger and distracting the two vertebrae; removing a damaged disc from between the two vertebrae; and inserting an implant through the clear passageway and placing the implant between the two vertebrae. An apparatus includes a tray having a base, a first side wall, a second side wall, a distal end and a proximal end, and wherein the base, the first side wall, and the second side wall define a passageway; at least one first finger coupled to the distal end of the tray; at least one second finger coupled to the distal end of the tray; at least one pull nut coupled to the proximal end of the tray; and wherein rotation of the at least one pull nut adjusts a distance between the at least one first finger and the at least one second finger.

20 Claims, 11 Drawing Sheets

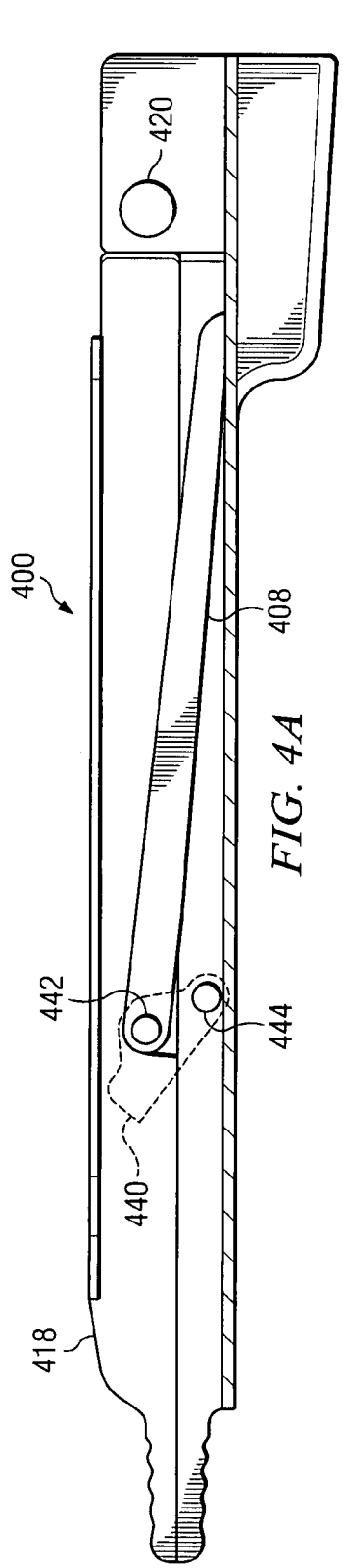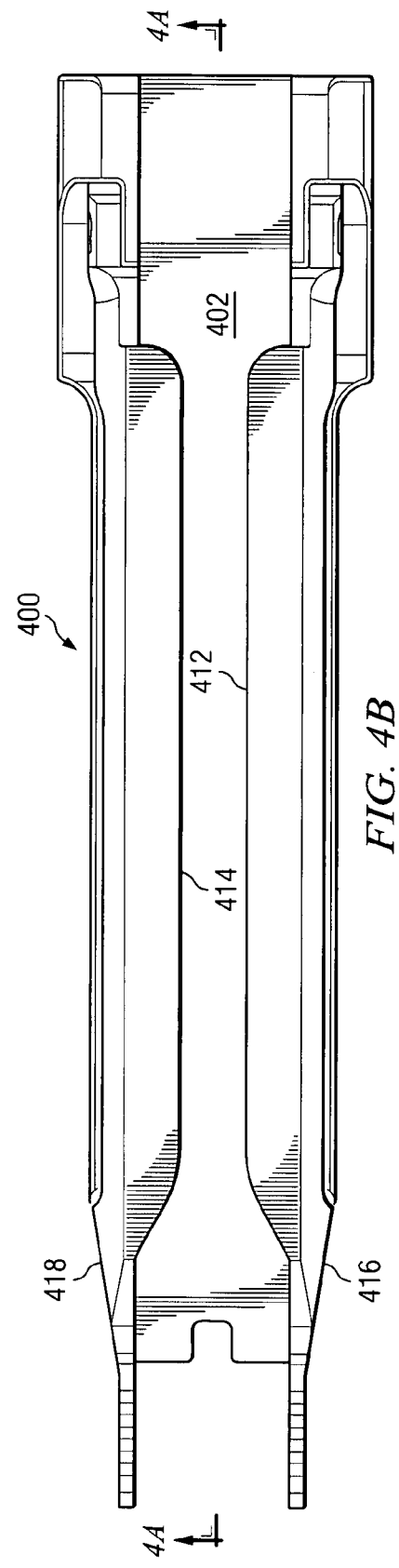

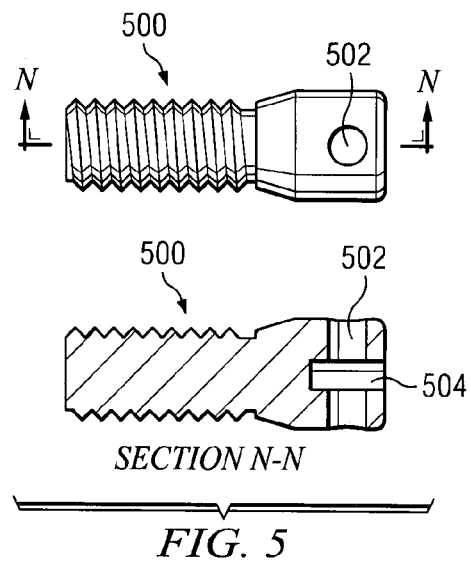
FIG. 5
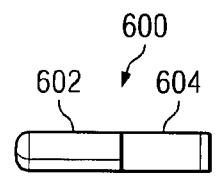
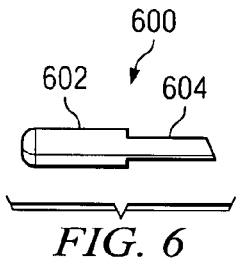
FIG. 6
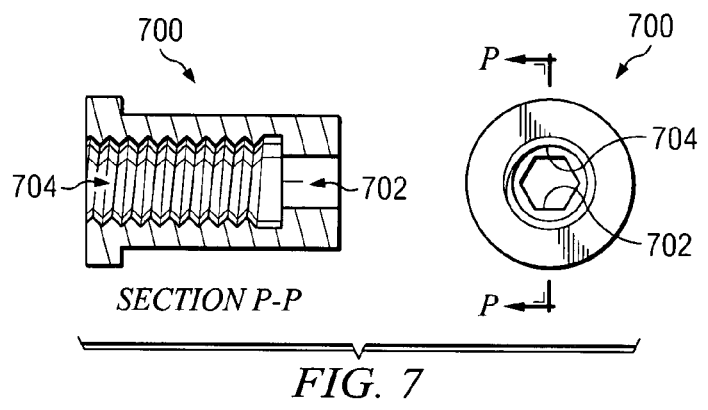
FIG. 7

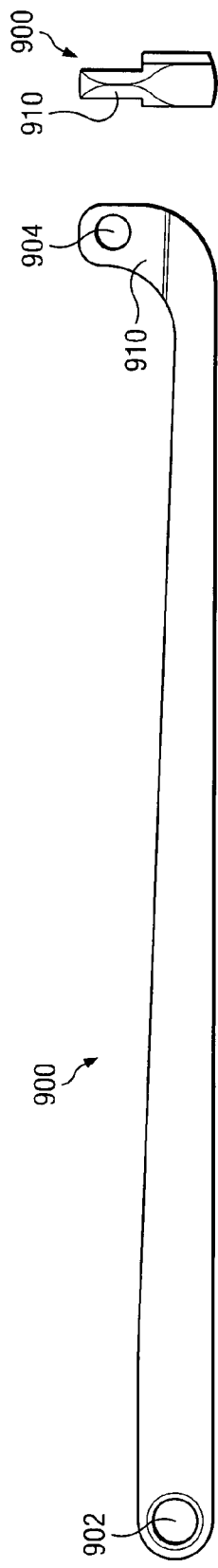
FIG. 9B
FIG. 9A
FIG. 9C
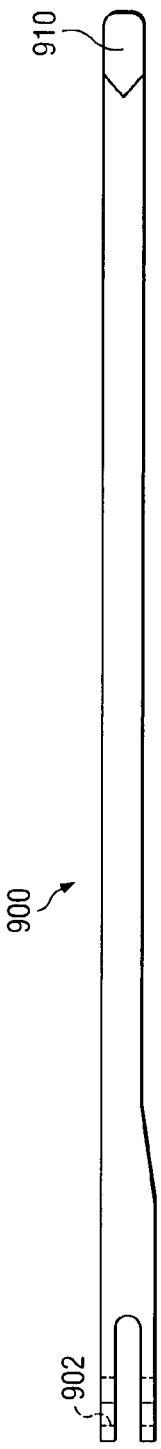
FIG. 10B
FIG. 10A
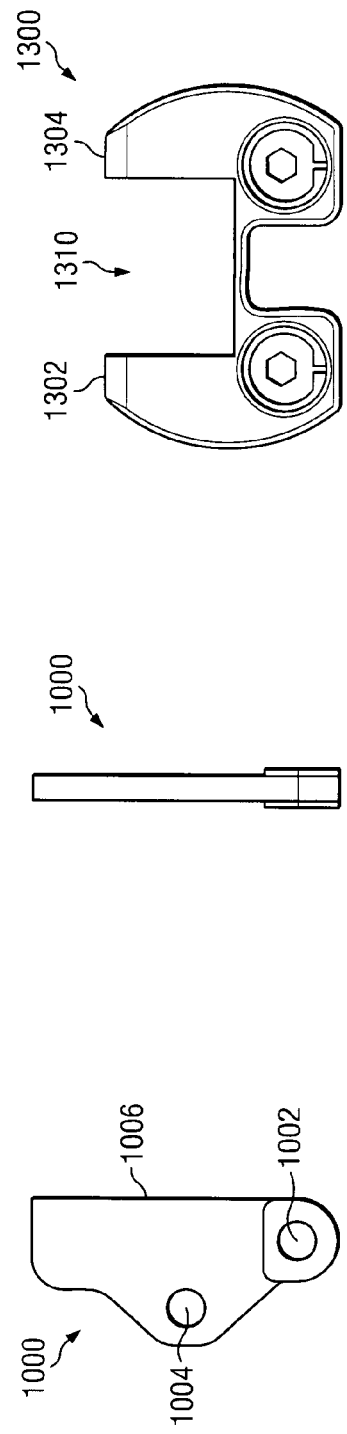
FIG. 13C

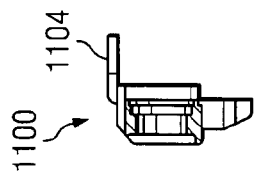
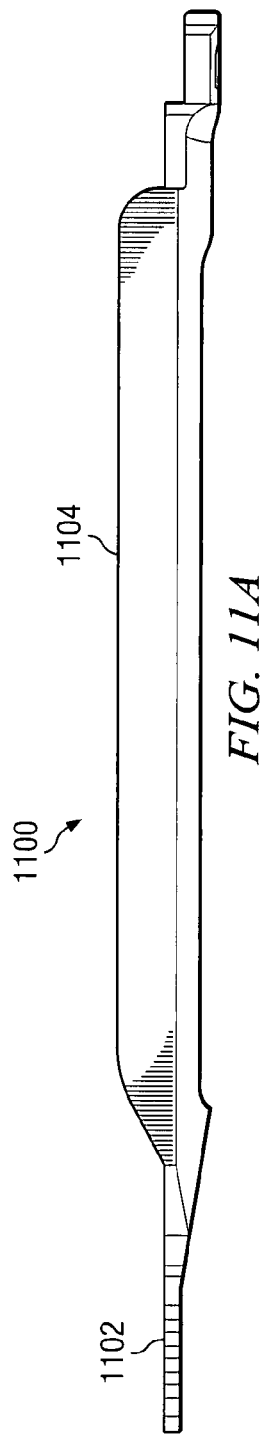
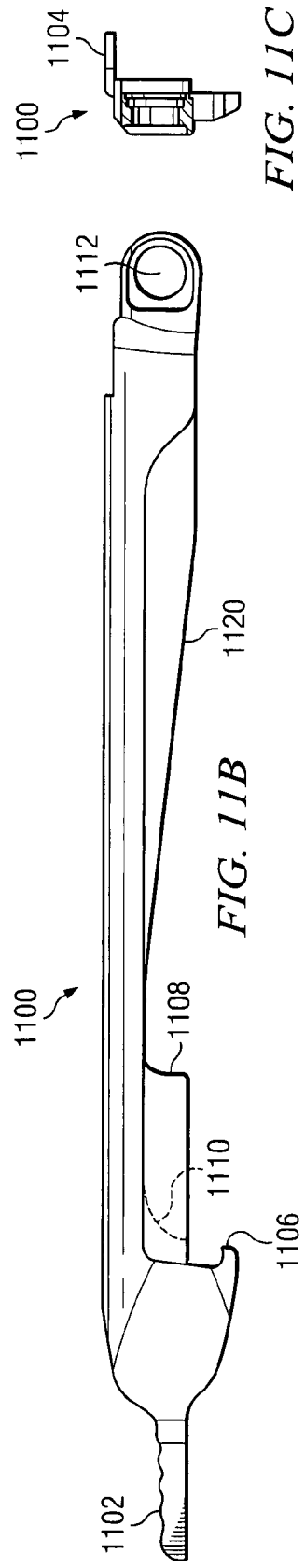

ANTERIOR SPINAL INTERBODY FUSION DELIVERY SYSTEM

BACKGROUND INFORMATION

1. Field of the Invention

Embodiments of the invention relate generally to the field of surgical instruments. More particularly, an embodiment of the invention relates to a spinal distraction and graft delivery system, and methods of using said system.

2. Discussion of the Related Art

Intravertebral discs, which separate and cushion the individual vertebrae of the human spine from each other, allow for the flexibility of the spine while still providing structural support. The intravertebral discs are often subject to degeneration with age, resulting in herniations, displacements, or other dysfunctions, thereby causing severe pain and lowering the quality of life. Artificial disc surgery, one preferred method of addressing this problem, involves the removal of the damaged disc and replacing it with an implant. This requires a surgical procedure in which the vertebrae adjacent to the damaged disc are separated (distracted), the damaged disc is removed, and an implant is positioned into the space between the distracted device.

Prior art spinal distraction instruments and spinal implant insertion instruments are known to those skilled in the art. For instance, a conventional spinal distraction device typically consists of two first class levers, hinged together to provide a spreading force at the distal end placed between the vertebrae when a spreading force is applied at the proximal end. Such a distraction device functions similarly to a pair of pliers.

A problem with this technology has been the danger of damaging surrounding soft tissues, especially the vulnerable nerve roots, during the distraction and implantation procedure. Therefore, what is required is solution that protects the soft tissue from being pinched or damaged.

Another problem with this technology has been that a clear passageway for the implantable procedure is not defined. Therefore, what is also required is a solution that provides for a clear implantation path while the vertebrae remain in a distracted position without significant obstruction of the working space. This also allows for a much shorter surgical procedure due to a more efficient means of implantation.

One unsatisfactory approach, in an attempt to solve the above-discussed problems is shown in FIGS. 1A and 1B, which shows a conventional distraction and implantation surgical device 100.

Device 100 consists of two arms 102 and 104, each ending in a pair of fingers, 106, and 108, respectively. The fingers are inserted between two vertebrae, and distraction occurs by applying squeezing pressure between the lower arm 104 and a third arm 110 shown in FIG. 1B. The force is transferred to the upper arm through projection 112, resulting in the separation of fingers 106 and 108, and in turn the distraction of the spine. However, a disadvantage of this approach is that it does not adequately protect the soft tissues from damage.

Another disadvantage of the conventional instrument shown in FIGS. 1A-1B is the inability to finely tune the distraction distance and to adjust for spinal curvature during the distraction of the vertebrae. Therefore, what is also needed is a solution that addresses these needed functions.

Heretofore, the requirements of protecting the soft tissues from damage during distraction of the vertebrae and the implantation of a graft, providing a clear implantation path, and providing a finely tunable distraction that is able to adjust for spinal curvature referred to above have not been fully met in a surgical instrument. What is needed is a solution that simultaneously solves all of these problems.

SUMMARY OF THE INVENTION

There is a need for the following embodiments of the invention. Of course, the invention is not limited to these embodiments.

According to an embodiment of the invention, a machine comprises: a tray having a base, a first side wall, a second side wall, a distal end and a proximal end, and wherein the base, the first side wall, and the second side wall define a passageway; at least one first finger coupled to the distal end of the tray; at least one second finger coupled to the distal end of the tray; and at least one pull nut coupled to the proximal end of the tray; wherein rotation of the at least one pull nut adjusts a distance between the at least one first finger and the at least one second finger.

According to another embodiment of the invention, a machine comprises: a tray having a base, a first side wall, a second side wall and defining a longitudinal place window, a distal end and a proximal end; a pair of serrated fingers located at the distal end of the tray, the pair of serrated fingers defining a plane; a first pull nut coupled to the first top arm, the first pull nut located at the proximal end of the tray; a first pull pin coupled to the first pull nut; a first draw arm coupled to the first pull pin; a first lift arm coupled to the first draw arm; a first top arm coupled to the first lift arm, the first top arm including a first independently adjustable serrated finger located at the distal end of the tray and a first flange that partially covers the longitudinal place window, wherein rotation of the first pull nut adjusts a first distance between the first independently adjustable serrated finger and the plane; a second pull nut coupled to the second top arm, the second pull nut located at the proximal end of the tray; a second pull pin coupled to the first pull nut; a second draw arm coupled to the second pull pin; a second lift arm coupled to the second draw arm; and a second top arm coupled to the second lift arm, the second top arm including a second independently adjustable serrated finger located at the distal end of the tray and a second flange that partially covers the longitudinal place window, wherein rotation of the second pull nut adjusts a second distance between the second independently adjustable serrated finger and the plane.

According to another embodiment of the invention, a process comprises: providing a surgical instrument comprising a clear passageway, a first stationary finger, a first adjustable finger, and a first pull nut; inserting the first stationary finger and the first adjustable finger between two vertebrae; rotating the first pull nut with a hex drive, thereby separating the first adjustable finger from the first stationary finger and distracting the two vertebrae; removing a damaged disc from between the two vertebrae; inserting an implant through the clear passageway and placing the implant between the two vertebrae.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of an embodiment of the invention without departing from the spirit thereof, and embodiments of the invention include all such substitutions, modifications, additions and/or rearrangements.

BRIEF DESCRIPTION OF THE DRAWINGS

The drawings accompanying and forming part of this specification are included to depict certain embodiments of the invention. A clearer conception of embodiments of the invention, and of the components combinable with, and operation of systems provided with, embodiments of the invention, will become more readily apparent by referring to the exemplary, and therefore nonlimiting, embodiments illustrated in the drawings, wherein identical reference numerals (if they occur in more than one view) designate the same elements. Embodiments of the invention may be better understood by reference to one or more of these drawings in combination with the description presented herein. It should be noted that the features illustrated in the drawings are not necessarily drawn to scale.

FIGS. 4A-4E show various views of the complete device, representing an embodiment of the invention.

FIG. 5 shows the pull pin of one embodiment of the invention

FIG. 6 shows the step pin of one embodiment of the invention

FIG. 7 shows the pull nut of one embodiment of the invention

FIGS. 9A-9C show various views of the draw arm of one embodiment of the invention FIGS. 10A-10B show two views of the lift arm of one embodiment of the invention FIGS. 11A-11C show several views of the top arm of one embodiment of the invention FIGS. 13A-13C shows several views of a third embodiment of the invention

DESCRIPTION OF PREFERRED EMBODIMENTS

Embodiments of the invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the embodiments of the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure. In general, the term 'proximal' refers to the location closer to the operator of the device when using the device of the invention according to the method of the invention, while the term 'distal' refers to the location further away from the operator of the device.

In general, the invention pertains to a surgical instrument. The surgical instrument of the present invention, sometimes called a graft tray, functions as an anterior spinal interbody fusion (ASIF) delivery system. The instrument provides for clear access between vertebrae, for the insertion of implantable grafts. The access is provided by inserting pairs of displaceable fingers between vertebrae and distracting the vertebrae by displacing the fingers through a rotational force applied at the proximal end of the instrument. The instrument includes a clear passageway to the distracted space which provides access to the intravertebral space for the removal of a damaged disc, preparation of the disc space and the insertion of a graft. The implantable graft may be, for example, a femur graft (irregular disc shaped), a cylindrical graft, or a conical graft. The shape and surfaces of the graft tray are designed to protect the surrounding tissues, such as the vulnerable nerve roots, from being pinched or otherwise damaged while providing such a clear passageway. The instrument may be used for operation on either the cervical, thoracic, or lumbar sections of the human spine.

Figure 2A:
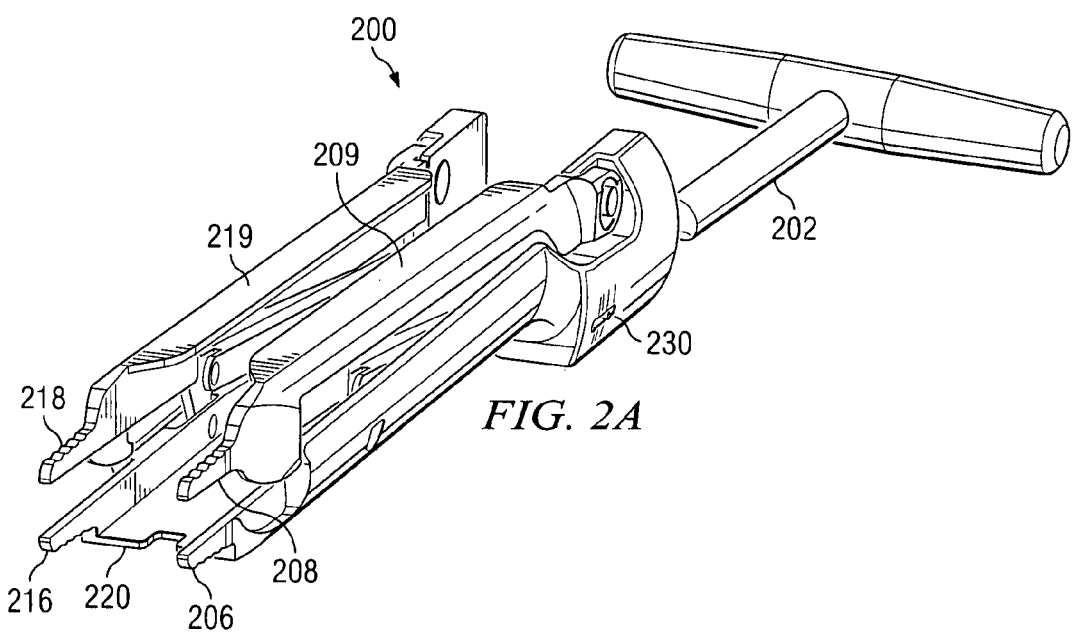
FIGS. 2A and 2B show two views of a preferred embodiment of the invention
Figure 2B:
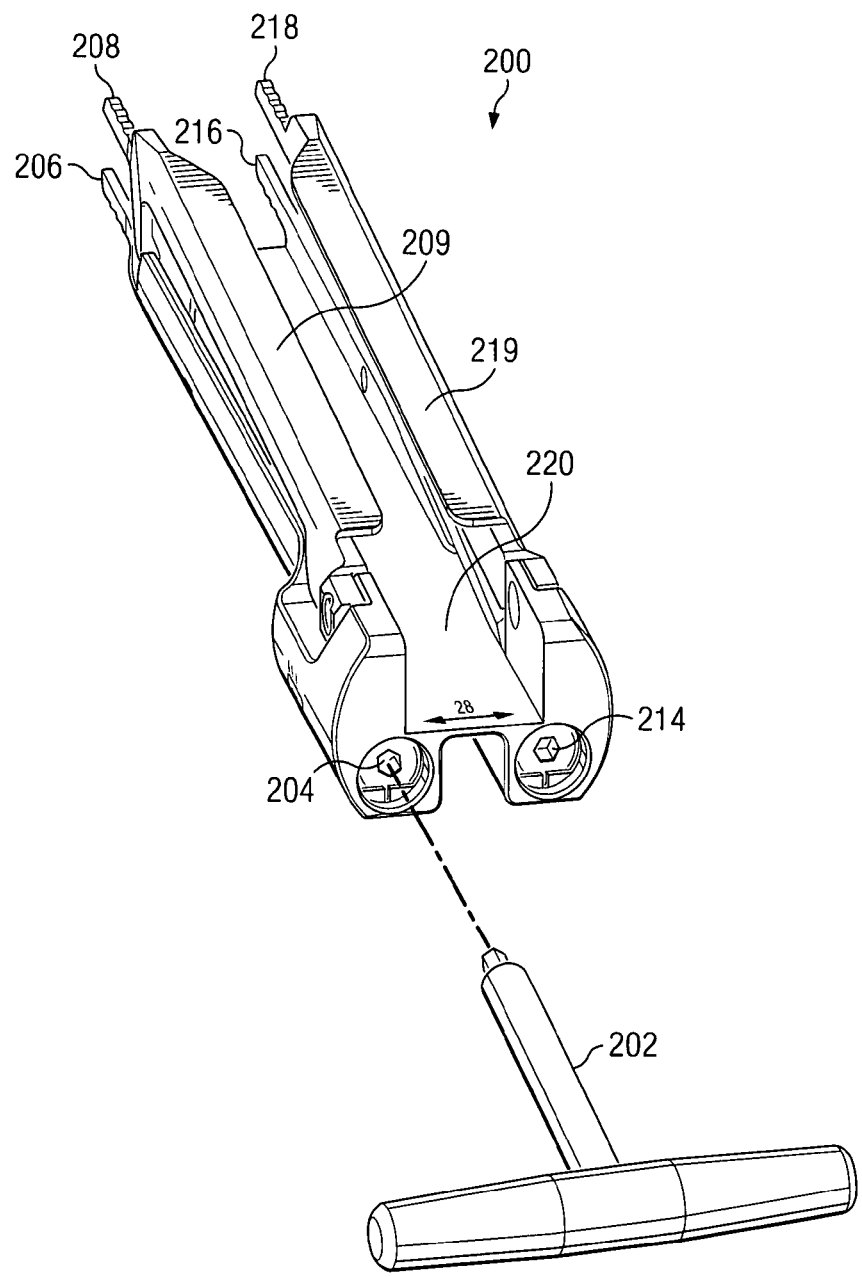

FIGS. 2A and 2B show two perspective views of the complete instrument 200 of a preferred embodiment of the invention. The instrument is operated with a hex drive 202, which is mated to fit inside the two hex-keyed pull nuts, left pull nut 204 and right pull nut 214 (shown in FIG. 2B), located at the proximal end of the instrument 200. Two pairs of serrated fingers are located at the distal end of the device. The serrations provide stability of the instrument in place during surgery. The first pair of fingers, left stationary finger 206, and right stationary finger 216, are stationary with respect to the tray (sometimes called the base) 220 of the instrument. The adjustable left finger 208 is coupled to the adjustable left top arm 209, and adjustable right finger 218 is coupled to the adjustable right top arm 219. The two top arms 209 and 219 are each displaceable with relation to the base 220. Rotation of the left pull nut 204 by turning the hex drive 202 leads to the displacement of the left top arm 209, which leads to the separation of the left adjustable finger 208 from the left stationary finger 206. Likewise, rotation of the right pull nut 214 by turning the hex drive 202 leads to the displacement of the right top arm 219, which leads to the separation of the right adjustable finger 218 from the right stationary finger 216.

The overall outside shape of the instrument is cylindrical, with a tapered entry end. This shape is for ease of use, ergonomic shape that fits well into the hand and prevents any tearing of the surgeon's glove. The tapered end minimizes the size of the incision and helps to bypass all the internal nerves, blood vessels, and other soft tissues sensitive to damage. In addition, smooth side walls and the internally contained distracting mechanism further helps to protect vulnerable surrounding soft structures during the surgical procedure. The smooth sliding surface inside the access passageway allows for different forms, sizes, and materials to be implanted with ease into the intravertebral disc space.

Figure 3:
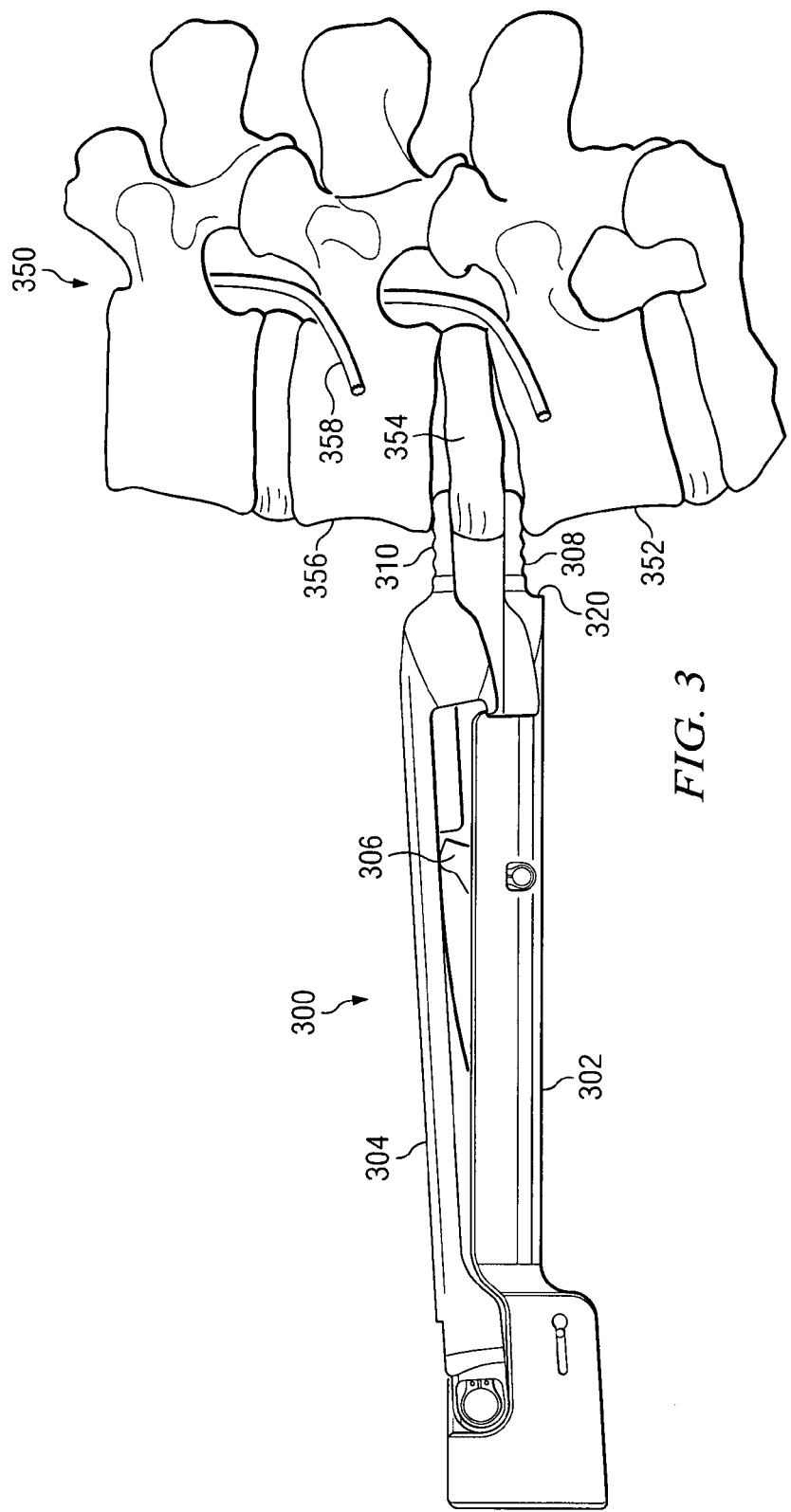
FIG. 3 illustrates one embodiment of a method of using the invention

FIG. 3 shows one embodiment of using the invention. The instrument 300 is positioned anteriorly to the spine 350. Stationary fingers 308 and movable fingers are inserted between vertebra 352 and 356. Vertebra 352 may be, for example, L5 (the fifth lumbar vertebra), and vertebra 356 may be L4 (the fourth lumbar vertebra). By using the hex drive to turn the left and right pull nuts (not shown in FIG. 3), the left and right top arms 304 are lifted from the tray 302 by the left and right lift arms 306. This separates the fingers 308 and 310 and distracts vertebra 352 and 356 from each other, without damaging any nerve roots 358. The distraction distances of the left and right movable fingers are independently adjusted. After distracting the vertebrae, the damaged disc is removed by the surgeon from in-between the distracted vertebrae. The damaged disc may be removed through an access area located at the bottom front 320 of the graft tray. To facilitate the removal of the damaged disc, the bottom of the graft tray is located below the contact area of the stationary (bottom) fingers. Subsequently to the removal of the old disc and preparation of the intravertebral space, an implantable graft 354 is placed between the vertebrae, through the clear passageway provided by the tray 302, using, for example, thin forceps (not shown).

Figure 1A:
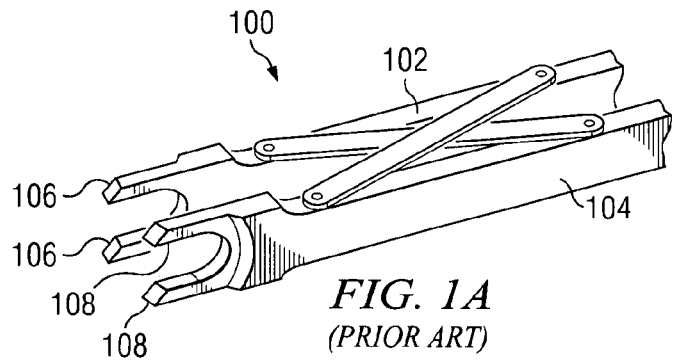
FIGS. 1A and 1B show two views of a conventional spinal distraction device, appropriately labeled "PRIOR ART."
Figure 1B:
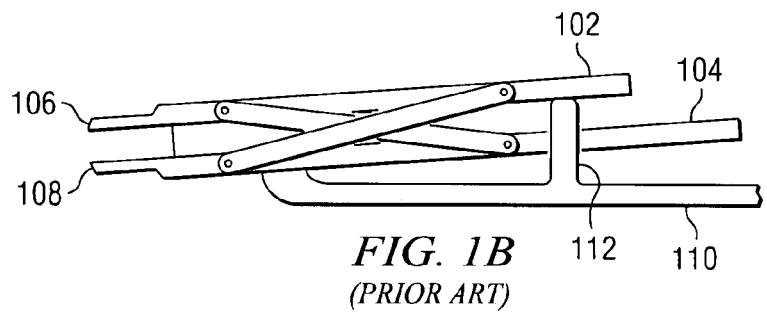

One of the key features of the invention is the ability to individually control the separation of the left pair of fingers 206 and 208 and the right pair of fingers 216 and 208. Conventional distraction instruments such as the one shown in FIGS. 1A and 1B lack this feature. Thus, the separation distance of the left pair of fingers 206 and 208 can be different from the separation distance of the right pair of fingers 216 and 218, and can vary over the whole range of distances available. For example, the left pair of fingers can be completely closed while the right pair of fingers remains completely open. This feature of the invention is essential, for example, when using the instrument 200 on a spine with a significant side bend. The ability to separately control the distraction distance of the left and right side is also useful in the implantation of irregularly shaped implantable grafts. The narrow serrated strong finger tips insert into the disc space and maximally distract the spine without significant obstruction of the working space for the surgeon. In addition, this device has a 470 measuring scale on both sides that is used to provide the surgeon the distraction opening for each independent pair of fingers.

Another key feature of the invention is the ability to finely tune the separation distance of the fingers through the use of the rotational hex drive. An optional measurement device 230 is shown in FIG. 2A, which measures the separation distance of the left pair of fingers. An identical measurement device (not shown) is located on the right side of the instrument. This allows the surgeon to achieve a desired distraction distance on each side. Such a desired distraction distance can be determined diagnostically before surgery.

In addition, it is easy for the surgeon to insert and turn the ergonomically designed hex drive and separate the fingers. The hex drive is removed after the desired separation distance is achieved. This makes the instrument easy to use during surgery and does not create unnecessary obstructions for the path of the implantation graft. The heavy and well balanced instrument frame combined with the serrated fingers allows the instrument to lock into place, and frees the assistant's and the surgeon's hands for other tasks. The instrument is easy to remove from the intravertebral space at the end of the procedure due to the easily collapsible fingers, by simply reversing the rotation of the pull nuts with the hex drive.

The preferred embodiment of the mechanism by which the pull nut activates and elevates the top arm 209 from the base 220 will now be described. The pull nut 204 has internal threads rotating freely in the instrument frame bore, threading onto a pull pin. The pull nut rotates in a stationary position during activation. The pull pin has external threads on one end and a through-slot on the other end to accommodate a draw arm, and the pull pin traverses along the axis of the pull nut during activation. The draw arm pivots in the pull pin at one end, and attaches to a lift arm at the other end. The draw arm is pulled along the axis of the pull pin as the pull pin traverses along the axis of the pull nut. The lift arm pivots in a fixed position on one end, being attached to the instrument frame. The other end of the lift arm makes contact with the underside of the top arm through a radial surface. The draw arm attaches midway to the lift arm, forcing the lift arm to rotate during activation while the draw arm is being pulled. The rotation of the lift arm forces the top arm to elevate from the base, thus separating the stationary and movable fingers. The pull pin, the draw arm, and the lift arm are not clearly visible in FIGS. 2A and 2B, but will be described in detail below with reference to the appropriate figures.

Figure 4C:
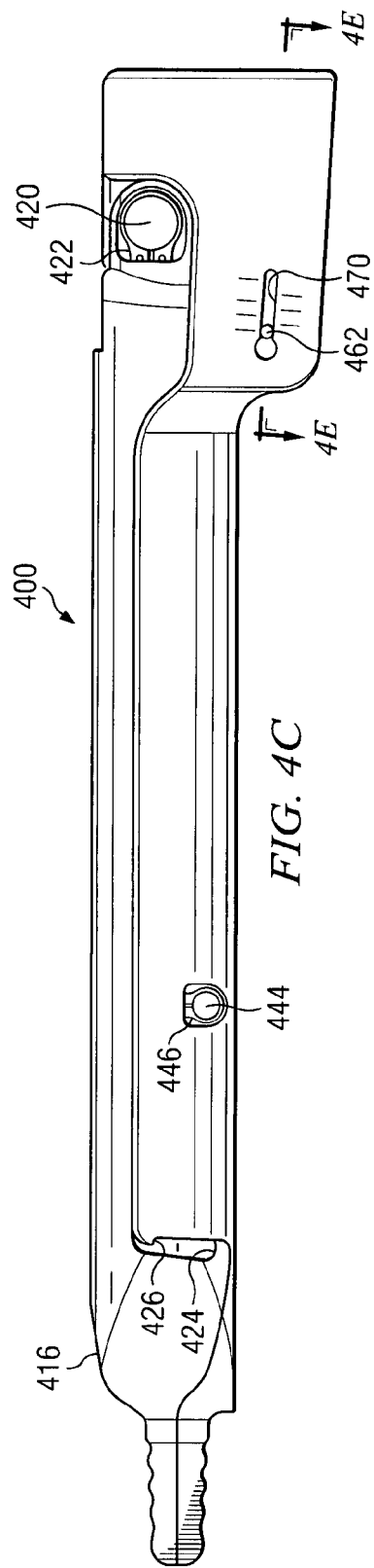
Figure 4E:
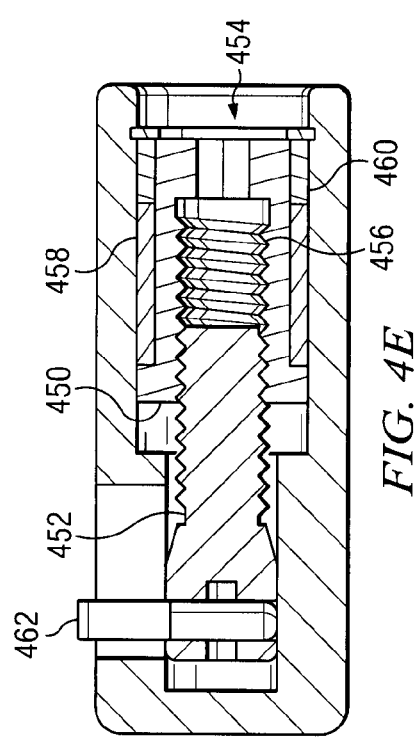
Figure 4D:
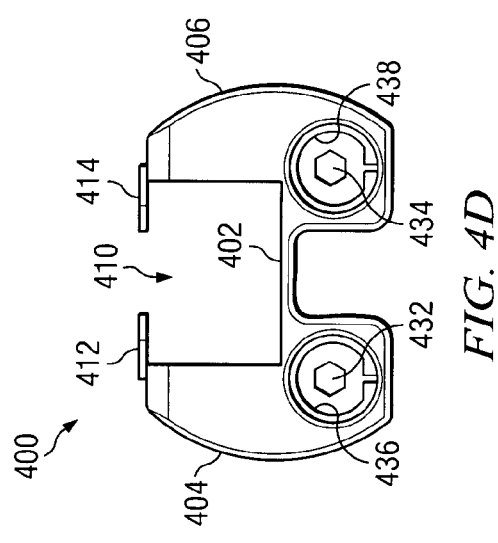

FIGS. 4A-4E show various views of the complete instrument. FIG. 4B shows the top view of the complete instrument. FIG. 4A shows the sectional view along section A-A of FIG. 4B. FIG. 4C shows the side view of the instrument, and FIG. 4D shows the end view of the instrument. Finally, FIG. 4E is the sectional view along section B-B of FIG. 4C.

The main frame, sometimes called the tray of the instrument 400, as shown in the end view of FIG. 4D, consists of the base 402, the left side wall 404, and the right side wall 406. Together, the base, the left side wall, and the right side wall, define a clear access path 410 for the implantable graft, the top of which has a longitudinal place window for monitoring the path of the graft. The upper boundary of the access path is defined by the left flange 412 of the left top arm 416, and the right flange 414 of the right top arm 418 (as shown in FIG. 4A). The partial covering of the top of this access path protects the access path from any intervening tissues, while providing a longitudinal place window which allows visual inspection of the path of the graft through the access path. FIG. 4D also shows the left pull nut 432 and right pull nut 434, which are held in place with left snap ring 436 and washer (not shown), and the right snap ring 438 and washer (not shown).

As can be seen in FIG. 4C, the top arm 416 is coupled to the instrument frame 400 through a pivot pin 420, around which the top arm is free to rotate. The pivot pin is secured with a snap ring 422 and a washer (not shown). The top arm has a lip 424, which engages a similar lip 426 of the left side wall of the frame 400, once the top arm is lifted past a certain height. This sets the maximum height to which the top arm can be lifted and prevent damage to the human spine from excessive distraction.

FIG. 4A shows the right draw arm in position. The right draw arm is attached to the right pull pin through a step pin (see FIG. 9B). The other end of the right draw arm is coupled to the right lift arm 440 through a right pivot pin 442. The right lift arm 440 is shown with a dotted line in FIG. 4A, because it is covered by the sides of the right top arm 418. The right lift arm is coupled to the instrument frame 400 through a right lift pin 444, which is secured with an external snap ring 446 (shown in FIG. 4C). When the pull pin pulls the draw arm proximally, the draw arm pulls on the lift arm through the pivot pin, which causes the lift arm to rotate around the lift pin and in turn lift the top arm. The left top arm, left draw arm, and left lift arm are coupled in the same manner.

FIG. 4E shows the details of section B-B of FIG. 4C, illustrating the pull nut 450 and the pull pin 452. In this case, the left pull nut and left pull pin are shown. The right pull nut and pull pin are coupled in the same manner. Details of the pull nut are shown in FIG. 5 and details of the pull pin are shown in FIG. 7. Applying the hex drive to the mated hex-keyed opening 454 causes the pull nut 450 to rotate. The internal threads 456 of the pull nut are mated with the external threads of the pull pin 452. The rotation of the pull nut causes the pull pin to traverse along its axis. The pull nut is coupled to a sleeve 458 to allow for smooth rotation in the instrument frame, and a stop sleeve 460, which prevent the pull nut from rotating past a maximum set distance. A step pin 462 is shown coupled to the pull pin 452. The step pin serves to couple the draw arm to the pull pin. The step pin also serves a measuring device by extending to the outside of the instrument frame and slides in a groove 470 (shown in FIG. 4C) in the instrument frame, which is marked with numbers. The measuring device, sometimes called the distraction gauge, indicates the separation distance of the fingers.

The pull pin 500 is shown in FIG. 5. The pull pin has a hole 502 transversely to its axis for accommodating the step pin. Slot 504 along the axis of the pull pin accommodates the draw arm, which secures the step pin into place.

The step pin 600 is shown in FIG. 6. The thicker section 602 of the step pin secures the draw arm to the pull pin and allows the draw arm to rotate around the step pin. The thin section of the pull pin 604 extends to the outside of the measurement frame and slides in a groove (item 470 in FIG. 4C) marked with numbers, which indicate the separation distance of the fingers.

The pull nut 700 is shown in FIG. 7. The hex-shape opening 702 is formed to accommodate a hex drive wrench. The hollow core 704 of the pull nut is lined with internal threads which match the external threads of the pull pin.

Figure 8A:
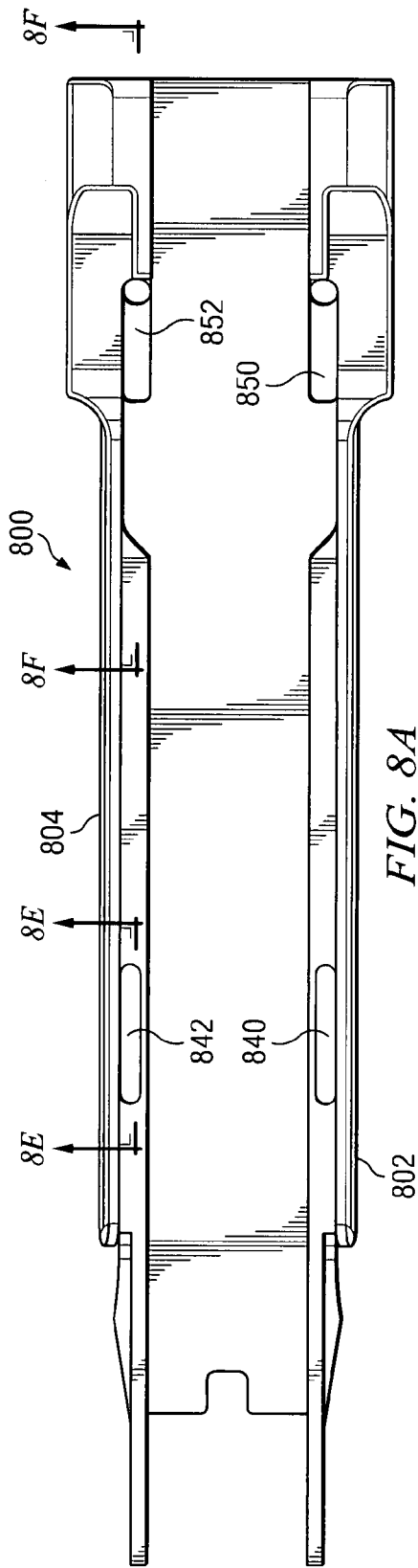
FIGS. 8A-8F show various views of the tray of one embodiment of the invention.
Figure 8B:
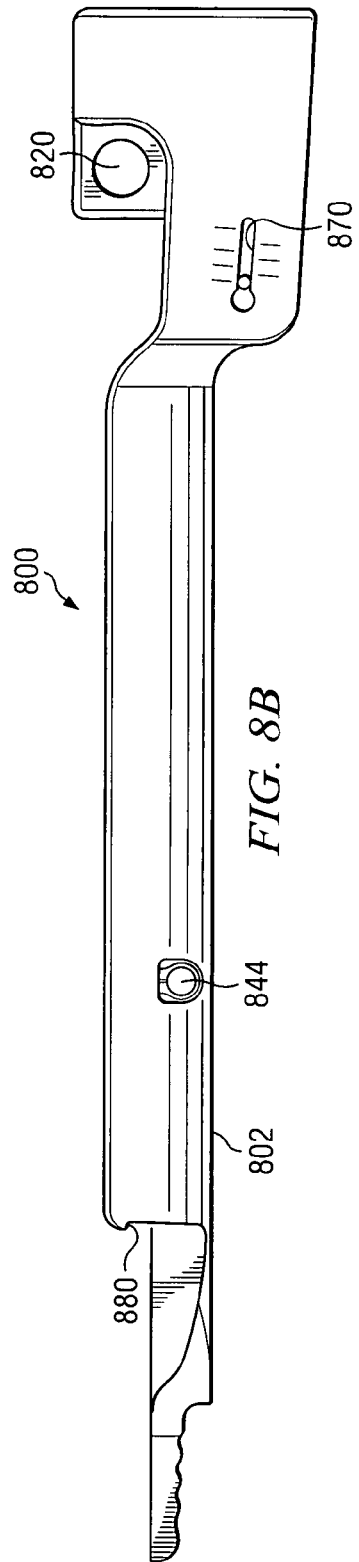
Figure 8C:
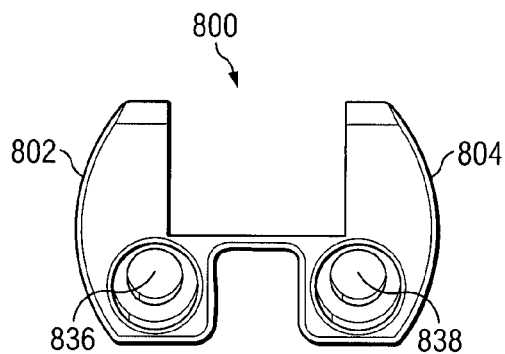
Figure 8D:
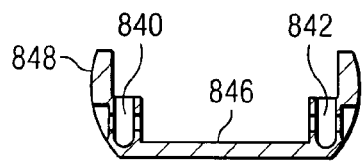
Figure 8E:
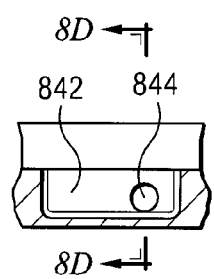
Figure 8F:
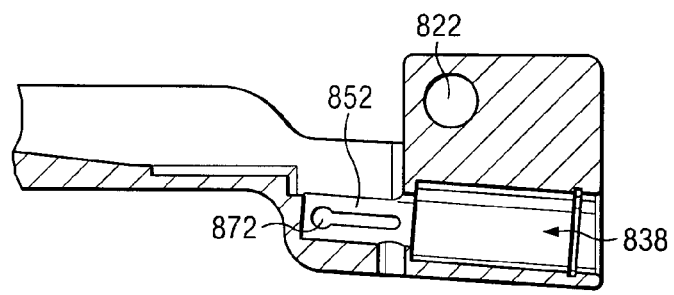

FIGS. 8A-8F show the instrument tray, sometimes called the instrument frame, without the top arms, lift arms, or draw arms. FIG. 8A shows the top view of the tray 800. FIG. 8B shows the side view of tray 800, and FIG. 8C shows the end view of the tray 800. FIG. 8F shows the sectional view of section C-C of FIG. 8A, FIG. 8E shows the sectional view of section D-D of FIG. 8A, and FIG. 8D shows the sectional view of section E-E of FIG. 8E.

The side view of FIG. 8B shows the left side wall 802, with opening 820 to accommodate the pivot pin which secures the top arm to the frame 800. The groove 870 is used as a measuring device, also referred to as the distraction gauge, by including a scale which indicates the position of the step pin. Though only the left distraction gauge 870 is shown in FIG. 8B, an identical gauge is present on the right side for measuring the distraction of the right top arm 804. Thus, the instrument frame has an independent distraction gauge for each top arm, which is used to measure the vertebrae distraction. Opening 844 accommodates the lift pin which secures the lift arm to the instrument frame. Lip 880 serves to contact a similar lip on the top arm and prevents the top arm from rising past the lip. The end view of FIG. 8C shows left opening 836 which accommodates the left hex nut and right opening 838, which accommodates the right hex nut.

FIG. 8F shows the sectional view of part of the right side wall of section C-C of FIG. 8A, showing the cylindrical opening 852, which accommodates the pull pin, and cylindrical opening 838, which accommodates the pull nut. Right opening 822 for the right pivot pin is also shown in FIG. 8F.

FIG. 8A shows the left cylindrical opening 850 for accommodating the left pull pin and the left draw arm which is coupled to the left pull pin, and the right cylindrical opening 852 for accommodating the right pull pin and the right draw arm which is coupled to the right pull pin. FIG. 8A also shows the left opening 840 for the left lift arm, and the right opening 842 for the right lift arm. FIG. 8E shows the sectional view D-D of FIG. 8A, illustrating the right opening 842 for the right draw arm and hole 846 for the right lift pin which secures the right lift arm to the instrument frame. FIG. 8D shows the sectional view of section E-E of FIG. 8E, showing another view of the left hole 840 for the left lift pin and the right hole 842 for the right lift pin.

FIG. 8D shows another key aspect of the invention. The bottom of the tray 846 is located below the position of the stationary fingers 848. This provides an access area for the surgeon to remove the damaged disc after distraction of the vertebrae and prior to the insertion of the graft. In one preferred embodiment, the graft tray bottom is 2 mm below the contact area of the stationary fingers.

FIG. 9A shows the side view of the draw arm 900. The draw arm is coupled to the pull pin through the step pin by opening 904 at the proximal end of the draw arm. The draw arm is coupled to the lift arm through the pivot pin by opening 902 at the distal end of the draw arm. As can be seen in FIG. 9A, the proximal end of the draw arm has a short protrusion 910. The protrusion 910 allows the draw arm to be coupled to the pull pin, which located lower in the instrument frame, and helps transfer the transverse motion of the pull pin, which is in the direction of the main axis of the pull pin and the instrument frame, into a motion that rotates the lift arm (see FIG. 4A for the position of the draw arm in the instrument frame). FIG. 9C shows the top view of the draw arm. The thin draw arm fits on top of the side wall of the instrument frame (see sidewalls 802 and 804 in FIG. 8A). FIG. 9B shows the end view of the lift arm.

FIG. 10A shows the lift arm in detail. The lift arm has two openings. Opening 1002 accommodates the lift pin, which secures the lift arm to the instrument frame. Opening 1004 accommodates the pivot pin, which couples the lift arm to the draw arm. The lift arm rotates around the lift pin as it lifts in a rotational motion. The curved upper surface 1006 of the lift arm contacts a similarly curved bottom surface of the top arm and elevates the top arm. FIG. 10B shows the side view of the lift arm, illustrating how the thin lift arm fits into the openings 840 or 842 shown in FIG. 8D.

FIG. 11A shows the top view of the top arm 1100 (in this case, the left top arm is shown). The flange 1104 can be seen in this figure, which serves to protect the access pathway formed by the base and side walls of the instrument frame. The distal end of the top arm ends in the adjustable finger 1102, which can be serrated for a more secure contact area. The flange 1104 can also be seen in the end view of FIG. 11C. FIG. 11B shows the side view, which illustrates the opening 1112, which couples the top arm to the instrument frame through a pivot pin. The top arm has two lips 1108 which descend down to cover the lift arm. The lift arm fits between these two lips and the curved surface of the lift arm (item 1006 in FIG. 10A) contacts the curved surface 1110 of the top arm. Lip 1106 serves to prevent the top arm from being elevated past a maximum distance by contacting a similar lip on the instrument frame (item 880 in FIG. 8B) and limits the maximum separation distance of the movable finger 1102 of the top arm and the stationary finger of the instrument frame. In addition, the top arm has an internal shield 1120. When the top arm is activated and thus in an elevated position, the internal shield 1120 spans the opening between the instrument frame and the top of the top arm. This protects the sides of the instrument and helps to maintain a clear passageway for graft insertion.

In a preferred embodiment, the passageway of the instrument is 28 mm wide, 20 mm high, and 240 mm long. In another preferred embodiment, the passageway of the instrument is 25 mm wide, 20 mm high, and 240 mm long. The dimensions of the passageway are determined by the size of the vertebrae of the patient and by the type of vertebrae being distracted. In one preferred embodiment, the size of each of the serrated fingers is 5 mm high, tapered to 4.5 mm high at the tip, and 2.5 mm thick.

Figure 12A:
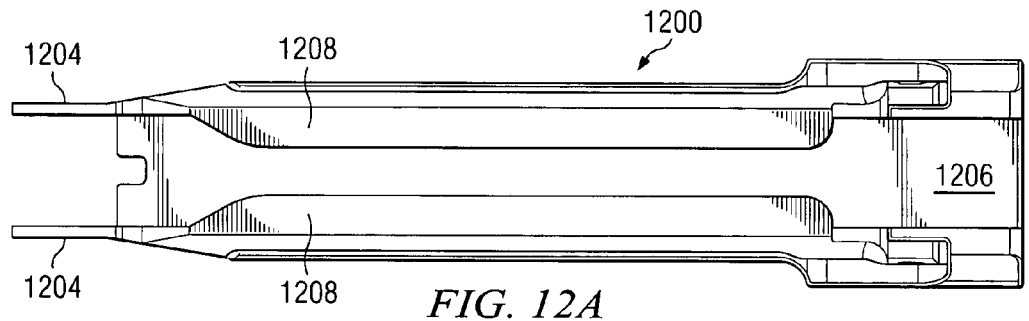
FIGS. 12A-12B show two views of a second embodiment of the invention
Figure 12B:
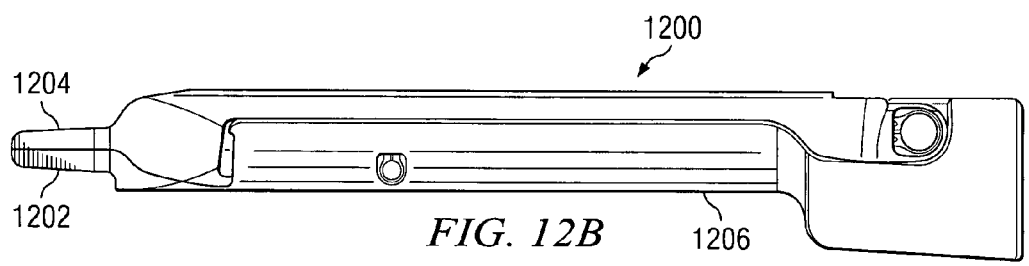

FIGS. 12A and 12B show a second embodiment of the invention and illustrate the complete instrument 1200. FIG. 12A shows the top view of instrument 1200 and FIG. 12B shows the side view of instrument 1200. In this embodiment, stationary fingers 1202 of the instrument frame 1206, and the movable fingers 1204 of the top arms 1208 are not serrated. In addition, there is no measurement device and therefore no groove in the instrument frame for the movement of the step pin, the step pin not extending into the side wall of the instrument frame.

This second embodiment of the invention is useful in applications when it is desirable to have a smoother outer surface of the instrument. Having smooth fingers without the serration and omitting the groove and extended step pin which form a measurement device provide for such a smoother outer surface and lessen the chance of snagging, pinching, or otherwise damaging delicate soft tissues while the instrument is being put into position.

Figure 13A:
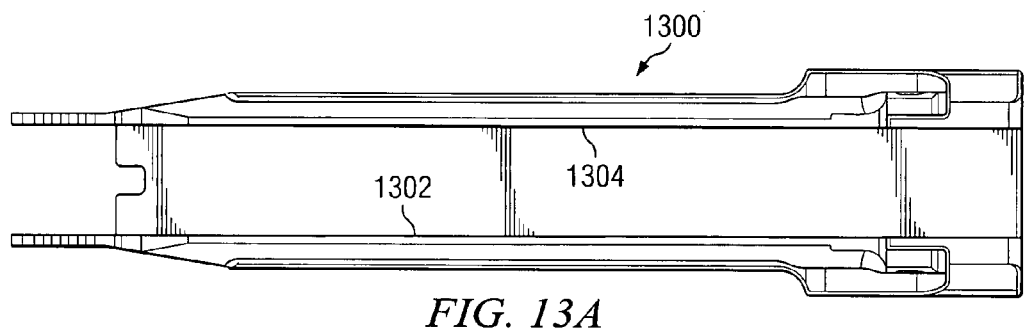
Figure 13B:
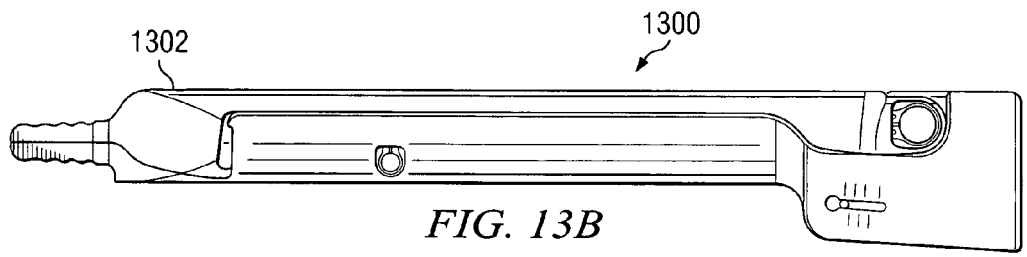

FIGS. 13A, 13B, and 13C show various views of a third embodiment of the invention and illustrate the complete instrument 1300. As can be see in FIG. 13A, which shows the top view of the instrument, neither the left top arm 1302 nor the right top arm 1304 have a flange. FIG. 13C shows the end view, where it can be seen that the longitudinal place window 1310 is not covered on top with a flange and thus remains larger along the whole length of the instrument.

The third embodiment of the invention is useful in applications where the access path for the implantation graft needs to remain more open and visible. This is useful when the graft is larger, has an irregular shape, or is more delicate, and the movement of the graft through the access path 1310 of FIG. 13C needs more space.

Alternately, in a fourth embodiment (not shown), the flanges of the top arms may extend all the way across and completely cover the longitudinal place window. In this embodiment, the clear passageway is completely protected from the top.

The particular material used for the ASIF surgical instrument should be a metal. Conveniently, the parts of an embodiment the invention can be made of any biocompatible metal material, such as, for example not by way of limitation, stainless steel, cobalt containing metals, or titanium. It is preferred that the material be stainless steel. One example of a biocompatible steel is type 316L, which contains a significant amount of nickel, which helps in resisting the corrosion resistance of chloride ions present in the human body. The use of an x-ray compatible metal such as stainless steel is preferred, as it allows for verification of the correct instrument placement during the surgical procedure.

In a preferred embodiment, the internal threads of the pull nut and the pull pin are made of dissimilar material for smooth activation. Preferably, the pull nut comprises stainless steel and the pull pin comprises a Co—Cr compound. Co—Cr compounds are known in the art to have smooth surfaces.

In a preferred embodiment, the main load bearing components of the ASIF surgical instrument are lined with a nonmetal material to prevent galling and achieve a smooth operation. Preferably, the nonmetal material is a polyetheretherketone (PEEK), which are well known in the art for their chemical resistance.

The surgical instrument of the present invention is thus made of a strong material that is easy to clean and repair and is reusable. The instrument is autoclaved before each use to sterilize it prior to the surgery.

However, the particular material selected for parts of the instrument is not essential to an embodiment of the invention, as long as it provides the described function. Normally, those who make or use an embodiment of the invention will select the best commercially available material based upon the economics of cost and availability, the expected application requirements of the final product, and the demands of the overall manufacturing process.

An embodiment of the invention can also be included in a kit-of-parts. The kit-of-parts can include some, or all, of the components that an embodiment of the invention includes. The kit-of-parts can be an in-the-field retrofit kit-of-parts to improve existing systems that are capable of incorporating an embodiment of the invention. The kit-of-parts can include software, firmware and/or hardware for carrying out an embodiment of the invention. The kit-of-parts can also contain instructions for practicing an embodiment of the invention. Unless otherwise specified, the components, software, firmware, hardware and/or instructions of the kit-of-parts can be the same as those used in an embodiment of the invention.

Definitions

The term substantially is intended to mean largely but not necessarily wholly that which is specified. The term approximately is intended to mean at least close to a given value (e.g., within 10% of). The term generally is intended to mean at least approaching a given state. The term coupled is intended to mean connected, although not necessarily directly, and not necessarily mechanically. The term proximate, as used herein, is intended to mean close, near adjacent and/or coincident; and includes spatial situations where specified functions and/or results (if any) can be carried out and/or achieved. The term deploying is intended to mean designing, building, shipping, installing and/or operating.

The terms first or one, and the phrases at least a first or at least one, are intended to mean the singular or the plural unless it is clear from the intrinsic text of this document that it is meant otherwise. The terms second or another, and the phrases at least a second or at least another, are intended to mean the singular or the plural unless it is clear from the intrinsic text of this document that it is meant otherwise. Unless expressly stated to the contrary in the intrinsic text of this document, the term or is intended to mean an inclusive or and not an exclusive or. Specifically, a condition A or B is satisfied by any one of the following: A is true (or present) and B is false (or not present), A is false (or not present) and B is true (or present), and both A and B are true (or present). The terms a or an are employed for grammatical style and merely for convenience.

The term plurality is intended to mean two or more than two. The term any is intended to mean all applicable members of a set or at least a subset of all applicable members of the set. The phrase any integer derivable therein is intended to mean an integer between the corresponding numbers recited in the specification. The phrase any range derivable therein is intended to mean any range within such corresponding numbers. The term means, when followed by the term "for" is intended to mean hardware, firmware and/or software for achieving a result. The term step, when followed by the term "for" is intended to mean a (sub)method, (sub)process and/or (sub)routine for achieving the recited result.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. The terms "consisting" (consists, consisted) and/or "composing" (composes, composed) are intended to mean closed language that does not leave the recited method, apparatus or composition to the inclusion of procedures, structure(s) and/or ingredient(s) other than those recited except for ancillaries, adjuncts and/or impurities ordinarily associated therewith. The recital of the term "essentially" along with the term "consisting" (consists, consisted) and/or "composing" (composes, composed), is intended to mean modified close language that leaves the recited method, apparatus and/or composition open only for the inclusion of unspecified procedure(s), structure(s) and/or ingredient(s) which do not materially affect the basic novel characteristics of the recited method, apparatus and/or composition.

Unless otherwise defined, all technical and scientific terms used herein have the same meaning as commonly understood by one of ordinary skill in the art to which this invention belongs. In case of conflict, the present specification, including definitions, will control.

Conclusion

The described embodiments and examples are illustrative only and not intended to be limiting. Although embodiments of the invention can be implemented separately, embodiments of the invention may be integrated into the system(s) with which they are associated. All the embodiments of the invention disclosed herein can be made and used without undue experimentation in light of the disclosure. Although the best mode of the invention contemplated by the inventor(s) is disclosed, embodiments of the invention are not limited thereto. Embodiments of the invention are not limited by theoretical statements (if any) recited herein. The individual steps of embodiments of the invention need not be performed in the disclosed manner, or combined in the disclosed sequences, but may be performed in any and all manner and/or combined in any and all sequences. The individual components of embodiments of the invention need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials.

It can be appreciated by those of ordinary skill in the art to which embodiments of the invention pertain that various substitutions, modifications, additions and/or rearrangements of the features of embodiments of the invention may be made without deviating from the spirit and/or scope of the underlying inventive concept. All the disclosed elements and features of each disclosed embodiment can be combined with, or substituted for, the disclosed elements and features of every other disclosed embodiment except where such elements or features are mutually exclusive. The spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A surgical instrument comprising:
   a tray having a base, a first side wall, a second side wall, a distal end and a proximal end, and wherein the base, the first side wall, and the second side wall define a passageway;
   at least one first stationary finger coupled to the distal end of the tray;
   at least one second stationary finger coupled to the distal end of the tray;
   at least one first top arm coupled near the proximal end of the tray, the first top arm having a first adjustable finger coupled to a distal end thereof;
   at least one second top arm coupled near the proximal end of the tray, the second top arm having a second adjustable finger coupled to a distal end thereof;
   adjustment members coupled near the proximal end of the tray;
   wherein the adjustment members displace the first top arm and second top arm, thereby adjusting a separation distance between the at least one first stationary finger and the first adjustable finger and the at least one second stationary finger and the second adjustable finger.

2. The surgical instrument of claim 1, wherein the adjustment members comprise a first pull nut and a second pull nut wherein a) rotation of the first pull nut displaces the first top arm, thereby adjusting a first separation distance between the at least one first stationary finger and the first adjustable finger and b) rotation of the second pull nut displaces the second top arm, thereby adjusting a second separation distance between the at least one second stationary finger and the second adjustable finger.

3. The surgical instrument of claim 1, wherein the first stationary finger, the second stationary finger, the first adjustable finger, and the second adjustable finger are serrated.

4. The surgical instrument of claim 1, wherein the first top arm and the second top arm define a longitudinal place window and wherein the first top arm comprises a first flange that partially covers the longitudinal place window and wherein the second top arm comprises a second flange that partially covers the longitudinal place window.

5. The surgical instrument of claim 2, further comprising a first pull pin coupled to the first pull nut, and a second pull pin coupled to the second pull nut.

6. The surgical instrument of claim 5, further comprising a first draw arm coupled to the first pull pin, and a second draw arm coupled to the second pull pin.

7. The surgical instrument of claim 6, further comprising a first lift arm coupled to the first draw arm, and a second lift arm coupled to the second draw arm.

8. The surgical instrument of claim 7, wherein the first top arm is coupled to the first lift arm and a second top arm is coupled to the second lift arm.

9. The surgical instrument of claim 2, further comprising a hex drive wrench which is mated to fit into the first pull nut and into the second pull nut.

10. The surgical instrument of claim 5, further comprising:
    a first distraction gauge, which indicates the distance between the first adjustable finger and the first stationary finger;
    a second distraction gauge, which indicates the distance between the second adjustable finger and the second stationary finger.

11. The surgical instrument of claim 10, wherein the first distraction gauge comprises a first step pin coupled to the first pull pin, and the second distraction gauge comprises a second step pin coupled to the second pull pin.

12. The surgical instrument of claim 8, wherein at least portions of exterior surfaces of the first top arm, the second top arm, and the tray are smooth, and wherein the tray is tapered toward the distal end of the tray.

13. The surgical instrument of claim 2, wherein the base of the tray is located a predetermined distance below the first stationary finger and the second stationary finger, to provide an access area for removing a damaged disc.

14. The surgical instrument of claim 8, wherein the surgical instrument comprises a metal selected from the group consisting of stainless steel, a cobalt-chromium alloy, and a titanium alloy.

15. The surgical instrument of claim 5, wherein the first pull pin and the second pull pin comprise a cobalt-chromium alloy and wherein the first pull nut and the second pull nut comprise a stainless steel.

16. The surgical instrument of claim 14, wherein the surgical instrument comprises a polyetheretherketone coating.

17. A method, comprising:
providing a surgical instrument, the surgical instrument comprising:
a clear passageway, a first stationary finger, a first adjustable arm having a first adjustable finger on a distal end thereof, wherein the clear passageway is defined by a tray having a base, a first side wall, a second side wall, a distal end and a proximal end;
a second stationary finger, a second adjustable arm having a second adjustable finger on a distal end thereof, and a second pull nut; and
adjustment members;
inserting the first stationary finger and the first adjustable finger between two vertebrae;
displacing the first top arm, thereby separating the first adjustable finger from the first stationary finger and distracting the two vertebrae;
removing a damaged disc from between the two vertebrae;
inserting an implant through the clear passageway and placing the implant between the two vertebrae.

18. The method of claim 17, further comprising:
inserting the second stationary finger and the second adjustable finger between the two vertebrae;
displacing the second top arm, thereby separating the second adjustable finger from the second stationary finger and distracting the two vertebrae;
wherein the separating the first adjustable finger from the first stationary finger results in a first separation distance and the separating the second adjustable finger from the second stationary finger results in a second separation distance.

19. An apparatus, comprising a surgical instrument including:
a tray having a base, a first side wall, a second side wall, a first top arm, a second top arm, and defining a longitudinal place window, a distal end and a proximal end;
a pair of serrated fingers located at the distal end of the tray, the pair of serrated fingers defining a plane;
a first pull nut coupled to the first top arm, the first pull nut located at the proximal end of the tray;
a first pull pin coupled to the first pull nut;
a first draw arm coupled to the first pull pin;
a first lift arm coupled to the first draw arm, wherein the first top arm is coupled to the first lift arm, the first top arm including a first independently adjustable serrated finger located at the distal end of the tray and a first flange that partially covers the longitudinal place window, wherein rotation of the first pull nut adjusts a first distance between the first independently adjustable serrated finger and the plane;
a second pull nut coupled to the second top arm, the second pull nut located at the proximal end of the tray;
a second pull pin coupled to the second pull nut;
a second draw arm coupled to the second pull pin;
a second lift arm coupled to the second draw arm;
a second top arm coupled to the second lift arm, the second top arm including a second independently adjustable serrated finger located at the distal end of the tray and a second flange that partially covers the longitudinal place window, wherein rotation of the second pull nut adjusts a second distance between the second independently adjustable serrated finger and the plane.

20. The method of claim 17, wherein the adjustment members comprise a first pull nut and a second pull nut wherein a) rotation of the at least one pull nut displaces the first top arm, thereby adjusting a first separation distance between the at least one first stationary finger and the first adjustable finger and b) rotation of the second pull nut displaces the second top arm, thereby adjusting a second separation distance between the at least one second stationary finger and the second adjustable finger.

* * * * *